(12) United States Patent
Kaupp

(10) Patent No.: US 6,331,889 B1
(45) Date of Patent: Dec. 18, 2001

(54) METHOD FOR OPTICALLY INSPECTING AN INTERMEDIATE LAYER OF AN AT-LEAST THREE-LAYER, LARGE-AREA ARTICLE

(75) Inventor: Ansgar Kaupp, Ahrensburg (DE)

(73) Assignee: Basler AG, Ahrensburg (DE)

( * ) Notice: Subject to any disclaimer, the term of this patent is extended or adjusted under 35 U.S.C. 154(b) by 0 days.

(21) Appl. No.: 09/598,728

(22) Filed: Jun. 21, 2000

(30) Foreign Application Priority Data

Jun. 25, 1999 (DE) .............................. 199 29 118

(51) Int. Cl.[7] .................................... G01N 21/00
(52) U.S. Cl. .......................................... 356/239.1
(58) Field of Search ............... 356/239.1, 239.2, 356/239.7, 239.8, 237.1, 237.2, 237.3; 348/125, 127, 128; 369/44.14, 44.41, 53.14; 250/559.08, 559.4, 559.45; 365/200, 201

(56) References Cited

U.S. PATENT DOCUMENTS

| 4,145,758 | | 3/1979 | Drexler et al. ................... 365/200 |
| 4,850,695 | * | 7/1989 | Mikuriya ......................... 356/237.1 |
| 5,196,716 | * | 3/1993 | Moriya et al. .................. 356/239.1 |
| 5,268,735 | * | 12/1993 | Hayashi ............................ 356/239.1 |
| 5,293,538 | * | 3/1994 | Iwata et al. ....................... 356/239.1 |
| 5,459,330 | * | 10/1995 | Venaille et al. ................. 250/559.45 |
| 5,790,247 | * | 8/1998 | Henley et al. ................... 356/239.1 |

FOREIGN PATENT DOCUMENTS

| 2843584 | 4/1979 | (DE) . |
| 3006043 | 8/1981 | (DE) . |

* cited by examiner

*Primary Examiner*—Hoa Q. Pham
(74) *Attorney, Agent, or Firm*—Howson and Howson

(57) ABSTRACT

A method for the inspection of an article which has a relatively large surface-area and which has at least two opposing, partially transparent, outer layers and at least one intermediate layer located between the outer layers. In particular, the method is utilized to optically inspect optical data media, for instance, DVDs, having the above referenced multilayer structure. The opposing sides of the article are sensed with at least two optical receivers, and the data of the recorded image points of the one optical receiver is allocated to the data of the recorded image points of the other optical receiver in such a manner that the data of the opposing points of the article are allocated to each other and can be evaluated. An identification of a potential error in the intermediate layer is possible when the data of the opposing image points indicate an error in the case of both optical receivers.

20 Claims, 1 Drawing Sheet

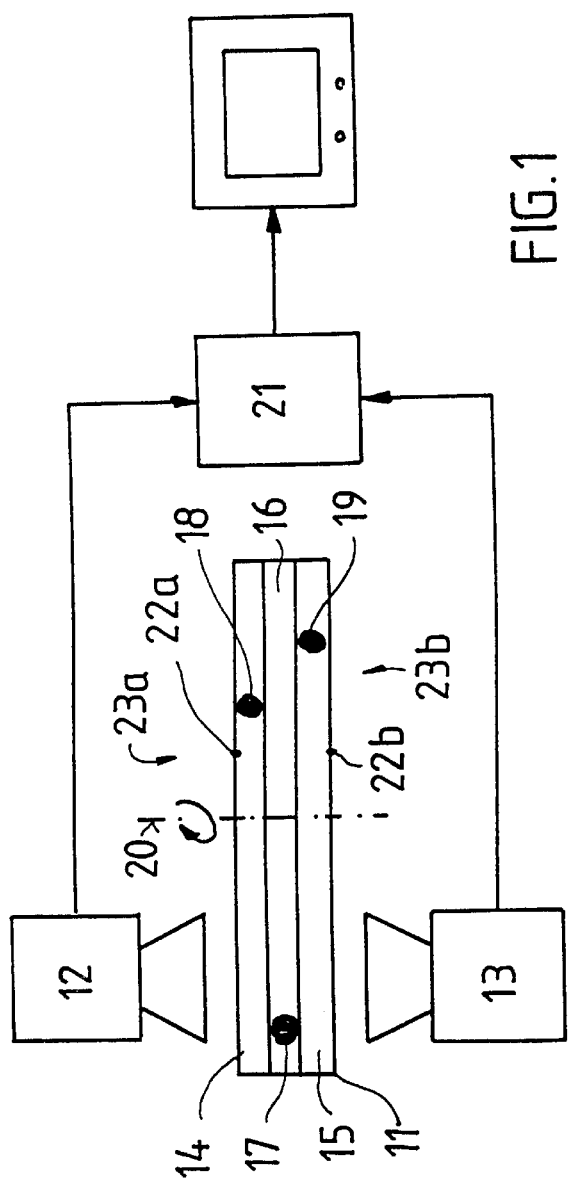
FIG. 1
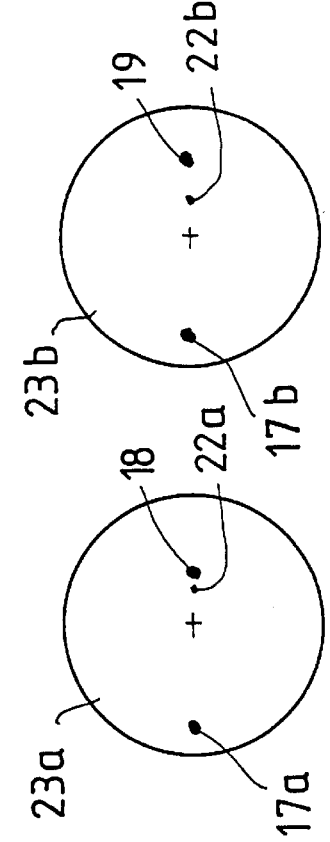
FIG. 2A  FIG. 2B
FIG. 3A  FIG. 3B

METHOD FOR OPTICALLY INSPECTING AN INTERMEDIATE LAYER OF AN AT-LEAST THREE-LAYER, LARGE-AREA ARTICLE

FIELD OF THE INVENTION

The invention pertains to a method for inspecting an essentially large-area article which consists of at least two opposing, partially-transparent, outer layers and at least one intermediate layer located between the outer layers. In particular, the invention pertains to the optical inspection of an optical data media, for example, a DVD, which has the above described three-layer structure. Therefore, hereinafter the discussion of the present invention pertains primarily to a DVD. However, it should be readily apparent that the method of the present invention is not necessarily restricted to use on that specific article.

BACKGROUND OF THE INVENTION

As is known, an optical data medium, such as a CD, DVD, CD-R or similar item, can be sensed optically and the data of the recorded image points can be evaluated in order to detect any potential flaws. In general, light is applied to the data side and is reflected from the reflecting layer of the optical data medium and shines on an optical receiver, for example, a CCD-camera. The light is often shaped as line light which extends across a radius of the data side of the optical data medium. The optical data medium is rotated about its rotational axis perpendicular to its flat sides so that, to check one entire side, at least one complete rotation of the data medium is required.

Only one data side is used on a CD so that this kind of sensing need be performed only from one side. However, in the case of a DVD, both opposing, flat sides are designed as data sides. In this case, checking of both sides is necessary. Basically, a DVD is configured such that it has two outer, transparent, plastic layers coated with a reflective layer and an adhesive layer provided as an intermediate layer which joins the two outer plastic layers together. Thus, a data medium is created which can be read on both sides.

In addition to checking the finished products for potential flaws, it is also necessary to classify the flaws, on the one hand, to handle certain flaws with more strict inspection criteria, and on the other hand, to allow a specific intervention in the on-going production process. This prevents additional flaws from occurring during production. The essential factor in this case, among others, is to recognize potential flaws in the intermediate layer, since these flaws will have an effect on both data sides.

The flaws in the intermediate layer are detectable from both sides. However, each optical receiver sees only the side of the intermediate layer which it faces. Thus, as a rule, a flaw in the intermediate layer cannot be classified as such solely due to its pattern.

OBJECT OF THE INVENTION

The invention is based on the problem of defining a method of the kind described above, so that a flaw in the intermediate layer will be reliably and dependably recognized as such.

SUMMARY OF THE INVENTION

According to this invention, the problem is solved by a method in which the opposing sides of the article are optically sensed with at least two optical receivers. The data of the recorded image points of the one optical receiver are allocated to the data of the recorded image points of the other optical receiver in such a manner that the data of the opposing points of the article are allocated to each other and can be evaluated. The identification of a potential error in the intermediate layer takes place when the data of the opposing image points indicate an error in the case of both optical receivers. This has the advantage that the opposing image points will be handled as such, and their data can be evaluated accordingly. If both data sets of the mutually opposing points have values that correspond to a flaw, then it has to be assumed that this flaw is located in the intermediate layer. Thus, the flaw will be identified immediately as a flaw in the intermediate layer and can be further evaluated accordingly.

In particular, it is possible, in the case of a potential detected flaw in the intermediate layer, to specify another, in particular a smaller fault tolerance in the course of the evaluation, than for other flaws. Thus, the inspection method can operate more precisely. The entire test method thus has a better effectiveness (yield), since the other flaws need not be handled with the same, more stringent test conditions.

In accordance with one design format of the invention, it is possible that the optical receivers or the recorded images have a predefined, relative alignment to each other or to a reference position, where the allocation of the data of the recorded image points takes place by a transformation of the geometric data with respect to the relative alignment to each other or to the reference position. Accordingly, the allocation can be a coordinate transformation which can be carried out quickly and easily. Typically, the coordinate transformation will be restricted to an offset. In this regard, it can be expedient to use the alignment of an optical receiver as a reference position so that only the data of the image points of the other optical receiver is required to be transformed.

Basically, the optical sensing can be carried out by both optical receivers simultaneously. In this case, the article is located on only one test station so that for a simultaneous sensing of the one or of the other side, a geometric allocation of the image points of both sides is readily possible. Thus the article to be tested cannot undergo any additional movements or rotations which will not be reliably ascertained and which would render an allocation of the opposing points impossible. Thus, the image points located on opposing sides always have an unambiguous geometric relation.

It is also useful to configure the optical receivers synchronously in such a manner that opposing points of the article are sensed simultaneously. The data of the image points of the opposing points of the article can then be compared at the same time, and any potential flaw in the intermediate layer can then be marked as such, possibly before its actual evaluation, so that the evaluation can be carried out with greater precision there, or the evaluation can be conducted with other criteria.

It is also possible to sense opposing sides in a chronological or geometric sequence or in partial optical offset, where the recorded image data of the one side or of a region of this one side, are saved at least until the other side or the region of the opposing side corresponding to the sensed side or region has been sensed. Then, the image data of the mutually opposing points are allocated to each other and evaluated. A storage of the data of the image points, as a rule, is necessary anyway, so that little or no time will be lost by the transformation.

Optical receivers can be provided by electronic cameras with, for instance, a CD chip. CMOS sensors or similar sensors, can also be utilized. These light-sensitive chips feature a number of pixels. According to the invention, it is possible to have a design such that the optical receivers each have at least one light-sensitive element with a number of pixels, and are aligned so that opposing image points of the article are imaged on the same or mirror-imaged pixels of the light-sensitive elements of the optical receivers. Thus, the allocation of the data of the mutually opposing points can be simplified.

It may be expedient for at least one optical receiver to have a line-like, light-sensitive element. Here the determination of the relative alignment to each other, or to a reference position, can take place very easily. The transformation of the data can thus be implemented very easily. It is also possible that at least one optical receiver will have one matrix-like, light-sensitive element.

The allocation of the optical receivers with respect to the article is essentially random, as long as an unambiguous allocation is possible to each other and to the article. Therefore, it is helpful for the optical receivers to be located on opposing sides of the article. It is also possible to use mirror elements which guide the two sides of the article to optical receivers located side by side. However, the specific, detailed alignment and configuration of the optical receivers will depend primarily on the spatial conditions of the production line in which the inspection system is integrated.

BRIEF DESCRIPTION OF THE DRAWINGS

The invention will be explained in greater detail below based on the following schematic illustrations.

FIG. 1 is a schematic illustration of an inspection system according to the inspection method of the present invention;

FIGS. 2A and 2B are generated images of a circular article obtained by the method according to the present invention; and FIGS. 3A and 3B are generated images of a circular article obtained with a prior art method.

DETAILED DESCRIPTION OF THE PREFERRED METHOD

The device illustrated in the drawings for testing of an article 11 features two optical receivers 12, 13, which are located on opposing sides of the article. The optical receivers can be designed as electronic cameras. The article has two external, essentially transparent layers 14, 15 and a layer 16 located therebetween. The layer 16 can inherently consist of several layers. Basically, the structure is that of a DVD, for example, such that the outer plastic layers 14, 15 are each provided on the insides with a reflective layer (not illustrated in detail) which layers are held together via a middle adhesive layer that corresponds to the intermediate layer 16. In the case of other multiple layer articles, this intermediate layer can also be impermeable or reflective in whole or in part, or at least in the viewing direction of the optical sensing, so that a coordination of the opposing points is readily possible.

The drawings present schematically a flaw 17 in the intermediate layer 16, a flaw 18 in the outer layer 14, and a flaw 19 in the opposite outer layer 15. For inspection of the article, as a rule, it is illuminated by a line light (not shown) and rotated at least once about its rotation axis 20 perpendicular to the layers. Thus, both flat sides are fully sensed and can be imaged. For the evaluation as such, the imaging is not absolutely necessary, but helpful. The images also illustrate the method.

On the images of the flat sides, the flaws may appear, for example, as contrast points. In FIGS. 2A and 3A, one potential image of the side 23a recorded by the camera 12 is presented, while in FIGS. 2B and 3B, one potential image of the side 23b recorded by the camera 13 is presented.

According to FIGS. 3A and 3B, the recorded images of the cameras 12 and 13 are imaged and evaluated independently from each other. It is evident that the image 17a of the flaw 17 in the intermediate layer 16 taken by the one camera 12 is located in an arbitrary position according to FIG. 3A relative to the image 17b of the same flaw 17 taken by the other camera 13 according to FIG. 3B. Thus, the flaw appears like the other flaws 18 or 19 in outer layers 14 or 15. A dependable classification of this flaw 17 as a flaw of the intermediate layer 16 is evidently not possible.

For an unambiguous determination of a flaw 17 in the intermediate layer 16, the optical receivers 12, 13 are coupled via an allocation unit 21 in order to allocate the data of the image points of the recorded images, so that opposing points 22a and 22b of the article are recognized as such, are imaged and/or can be evaluated accordingly. Thus, the result is that the images 17a, 17b of the flaw 17 in the intermediate layer are located at the same position both due to the camera 12 and also due to the camera 13. This is illustrated in FIGS. 2A and 2B, and it is evident that the images 17a and 17b of the flaw 17 are coincident. Basically, a mirror-image allocation is possible.

It is evident that with the appearance of a flaw precisely, or essentially exactly, at the same location on both sides of the article, a flaw is present in the intermediate layer with a dependability bordering on certainty. Thus, the flaw can be recognized, classified and evaluated as such.

What is claimed is:

1. A method for inspecting a large-area article having at least two opposing outer layers (14, 15) which are at least partially transparent, and at least one intermediate layer (16) located between the outer layers, comprising the steps of:

optical sensing of opposing sides (23a, 23b) of the article (11) with at least two optical receivers (12, 13);

allocating data of recorded image points of one of said optical receivers (12) to data of recorded image points of the other of said optical receivers (13) so opposing points (22a, 22b) of the article are allocated to each other for evaluation; and identifying a potential error (17) in the intermediate layer (16) when said data of said opposing image points indicate an error in the case of both optical receivers.

2. A method according to claim 1, wherein said optical receivers have a predefined relative alignment to each other, and wherein said allocating of said data of recorded image points takes place by a transformation of geometric data with respect to said relative alignment.

3. A method according to claim 1, wherein said optical receivers have a predefined relative alignment to a reference position, and wherein said allocating of said data of recorded image points takes place by a transformation of geometric data with respect to said relative alignment to said reference position.

4. A method according to claim 1, wherein said recorded image points have a predefined relative alignment to each other, and wherein said allocating of said data of said recorded image points takes place by a transformation of geometric data with respect to said relative alignment.

5. A method according to claim 1, wherein said recorded image points have a predefined relative alignment to a reference position, and wherein said allocating of said data of said recorded image points takes place by a transformation of geometric data with respect to said relative alignment to said reference position.

6. A method according to claim 1, wherein said optical sensing by each of said optical receivers occurs simultaneously.

7. A method according to claim 1, wherein said optical receivers are configured synchronously to each other so that said opposing points of the article are sensed simultaneously.

8. A method according to claim 1, wherein said opposing sides (23a, 23b) are sensed in sequence, and wherein said data of recorded image points of at least a region of one of the opposing sides are saved at least until at least a corresponding region on the other of said opposing sides is sensed, and that then the image data of the mutually opposing recorded image points are allocated to each other and evaluated.

9. A method according to claim 8, wherein said opposing sides (23a, 23b) are sensed in chronological sequence.

10. A method according to claim 8, wherein said opposing sides (23a, 23b) are sensed in geometric sequence.

11. A method according to claim 8, wherein said opposing sides (23a, 23b) are sensed in partial optical offset.

12. A method according to claim 1, wherein the article is an optical data medium.

13. A method according to claim 12, wherein the article is a DVD.

14. A method according to claim 1, wherein the outer layers of the article are essentially transparent.

15. A method according to claim 1, wherein the intermediate layer has an at least partly reflecting layer.

16. A method according to claim 1, wherein said optical receivers each have at least one light-sensitive element with a number of pixels and are aligned so that said opposing points are imaged on the same corresponding pixels of the light-sensitive elements of each of said optical receivers.

17. A method according to claim 1, wherein said optical receivers each have at least one light-sensitive element with a number of pixels and are aligned so that said opposing points are imaged on corresponding mirror-imaged pixels of the light-sensitive elements of each of said optical receivers.

18. A method according to claim 1, wherein at least one optical receiver has a line-like, light-sensitive element.

19. A method according to claim 1, wherein at least one optical receiver has a matrix-like, light-sensitive element.

20. A method according to claim 1, wherein said optical receivers (12, 13) are located on opposing sides (23a, 23b) of the article (11).

* * * * *

UNITED STATES PATENT AND TRADEMARK OFFICE
CERTIFICATE OF CORRECTION

PATENT NO.     : 6,331,889 B1
DATED          : December 18, 2001
INVENTOR(S)    : Kaupp It is certified that error appears in the above-identified patent and that said Letters Patent is hereby corrected as shown below:

Column 4,
Line 43, "so opposing points" should be amended to read -- so that data of opposing points --.

Signed and Sealed this

Twenty-fifth Day of June, 2002

Attest:

Attesting Officer

JAMES E. ROGAN
Director of the United States Patent and Trademark Office